(12) United States Patent
Hyde et al.

(10) Patent No.: US 8,758,677 B2
(45) Date of Patent: Jun. 24, 2014

(54) STERILIZATION OF CONSUMABLE COMPOSITION DISPENSERS

(75) Inventors: Roderick A. Hyde, Redmond, WA (US);
Eric C. Leuthardt, St. Louis, MO (US);
Robert W. Lord, Seattle, WA (US);
Clarence T. Tegreene, Bellevue, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1547 days.

(21) Appl. No.: 12/006,252

(22) Filed: Dec. 31, 2007

(65) Prior Publication Data

US 2009/0169419 A1    Jul. 2, 2009

Related U.S. Application Data

(63) Continuation-in-part of application No. 11/998,461, filed on Nov. 29, 2007, and a continuation-in-part of application No. 12/001,061, filed on Dec. 7, 2007, and a continuation-in-part of application No. 12/001,063, filed on Dec. 7, 2007, now Pat. No. 7,804,419, and a continuation-in-part of application No. 12/002,794, filed on Dec. 18, 2007, and a continuation-in-part of application No. 12/004,094, filed on Dec. 19, 2007.

(51) Int. Cl.
*A61L 2/00* (2006.01)
*G06F 19/00* (2011.01)

(52) U.S. Cl.
CPC ........... *G06F 19/3462* (2013.01); *A61L 2/0005* (2013.01)
USPC ................. 422/1; 422/24; 700/240

(58) Field of Classification Search
USPC ........................ 422/24, 1; 700/240
See application file for complete search history.

(56) References Cited

U.S. PATENT DOCUMENTS

| | | |
|---|---|---|
| 4,223,801 A | 9/1980 | Carlson |
| 4,310,103 A | 1/1982 | Reilly, Jr. et al. |
| 4,641,692 A | 2/1987 | Bennett |
| 4,823,982 A | 4/1989 | Aten et al. |
| 4,899,839 A | 2/1990 | Dessertine et al. |
| 5,221,024 A | 6/1993 | Campbell |
| RE34,337 E | 8/1993 | Bennett |
| 5,329,459 A | 7/1994 | Kaufman et al. |
| 5,342,518 A | 8/1994 | Posner et al. |
| 5,372,276 A | 12/1994 | Daneshvar |
| 5,408,443 A | 4/1995 | Weinberger |
| 5,454,406 A | 10/1995 | Rejret et al. |
| 5,522,525 A | 6/1996 | McLaughlin et al. |
| 5,651,887 A | 7/1997 | Posner et al. |
| 5,681,507 A | 10/1997 | Kazuma |

(Continued)

OTHER PUBLICATIONS

U.S. Appl. No. 12/927,038, filed Nov. 4, 2010, Hyde et al.

(Continued)

*Primary Examiner* — Timothy Cleveland
(74) *Attorney, Agent, or Firm* — Suiter Swantz pc llo (57) ABSTRACT

Methods and systems for administering a consumable composition may provide for one or more operations including, but not limited to: obtaining schedule data specifying a consumable composition dose consumption schedule for a specified user; dispensing at least one dose of a consumable composition into a container according to the schedule data specifying a consumable composition dose consumption schedule for the specified user; and controlling sterilizing of at least a portion of the container.

18 Claims, 7 Drawing Sheets

(56) References Cited

U.S. PATENT DOCUMENTS

| | | |
|---|---|---|
| 5,752,621 A | 5/1998 | Passamante |
| 5,826,217 A | 10/1998 | Lerner |
| 5,850,344 A | 12/1998 | Conkright |
| 5,851,445 A | 12/1998 | Kazuma |
| 5,955,009 A | 9/1999 | Kazuma |
| 5,958,307 A | 9/1999 | Kazuma |
| 5,971,594 A | 10/1999 | Sahai et al. |
| 6,054,928 A | 4/2000 | Lemelson et al. |
| 6,068,156 A | 5/2000 | Liff et al. |
| 6,113,080 A | 9/2000 | Kazuma |
| 6,182,453 B1 | 2/2001 | Forsberg |
| 6,183,691 B1 | 2/2001 | Swank et al. |
| 6,249,717 B1 | 6/2001 | Nicholson et al. |
| 6,252,494 B1 | 6/2001 | Howell |
| 6,263,259 B1 | 7/2001 | Bartur |
| 6,304,797 B1 | 10/2001 | Shusterman |
| 6,330,957 B1 | 12/2001 | Bell-Greenstreet |
| 6,332,100 B1 | 12/2001 | Sahai et al. |
| 6,490,920 B1 | 12/2002 | Netzer |
| 6,529,801 B1 | 3/2003 | Rosenblum |
| 6,539,281 B2 | 3/2003 | Wan et al. |
| 6,604,650 B2 | 8/2003 | Sagar |
| 6,625,518 B2 | 9/2003 | Depeursinge |
| 6,636,780 B1 | 10/2003 | Haitin et al. |
| 6,684,920 B2 | 2/2004 | Seitz et al. |
| 6,697,704 B2 | 2/2004 | Rosenblum |
| 6,732,884 B2 | 5/2004 | Topliffe et al. |
| 6,766,218 B2 | 7/2004 | Rosenblum |
| 6,773,668 B1 | 8/2004 | Everson et al. |
| 6,801,123 B2 | 10/2004 | Brakus |
| 6,856,932 B1 | 2/2005 | Wallace |
| 6,892,941 B2 | 5/2005 | Rosenblum |
| 7,072,738 B2 | 7/2006 | Bonney et al. |
| 7,175,081 B2 | 2/2007 | Andreasson et al. |
| 7,295,890 B2 | 11/2007 | Jean-Pierre |
| 7,440,818 B2 | 10/2008 | Handfield et al. |
| 7,444,203 B2 | 10/2008 | Rosenblum |
| 7,454,267 B2 | 11/2008 | Bonney et al. |
| 7,469,820 B2 | 12/2008 | Rosenblum |
| 7,471,993 B2 | 12/2008 | Rosenblum |
| 7,502,664 B2 | 3/2009 | Berg |
| 7,516,082 B2 | 4/2009 | Sanville et al. |
| 7,630,791 B2 | 12/2009 | Nguyen et al. |
| 7,715,277 B2 | 5/2010 | de la Huerga |
| 7,774,097 B2 | 8/2010 | Rosenblum |
| 7,804,419 B2 | 9/2010 | Hyde et al. |
| 7,831,336 B2 | 11/2010 | Gumpert |
| 7,844,361 B2 | 11/2010 | Jean-Pierre |
| 7,907,477 B2 | 3/2011 | Puzia |
| 8,019,471 B2 | 9/2011 | Bogash et al. |
| 8,060,249 B2 | 11/2011 | Bear et al. |
| 8,068,015 B2 | 11/2011 | Burg |
| 8,116,907 B2 | 2/2012 | Hyde et al. |
| 8,195,330 B2 | 6/2012 | Coe |
| 8,325,011 B2 | 12/2012 | Butler et al. |
| 8,362,914 B2 | 1/2013 | Hyde et al. |
| 8,457,783 B2 | 6/2013 | Hyde et al. |
| 2001/0011501 A1 | 8/2001 | Sato et al. |
| 2001/0045242 A1 | 11/2001 | Clusserath et al. |
| 2002/0001535 A1 | 1/2002 | Weng |
| 2002/0088817 A1 | 7/2002 | Bell-Greenstreet |
| 2003/0050731 A1 | 3/2003 | Rosenblum |
| 2003/0084957 A1 | 5/2003 | Seitz et al. |
| 2003/0088332 A1 | 5/2003 | Rosenblum |
| 2003/0093181 A1 | 5/2003 | Rosenblum |
| 2003/0220608 A1 | 11/2003 | Huitt et al. |
| 2004/0163970 A1 | 8/2004 | Sin et al. |
| 2004/0164146 A1 | 8/2004 | Rosenblum |
| 2004/0215369 A1 | 10/2004 | Rosenblum |
| 2004/0249250 A1 | 12/2004 | McGee et al. |
| 2005/0065645 A1 | 3/2005 | Liff et al. |
| 2006/0097000 A1 | 5/2006 | Gumpert |
| 2006/0259195 A1* | 11/2006 | Eliuk et al. .................... 700/245 |
| 2006/0266763 A1 | 11/2006 | Svabo Bech |
| 2006/0283876 A1 | 12/2006 | Mocnik et al. |
| 2007/0145067 A1 | 6/2007 | Headlee |
| 2007/0184219 A1 | 8/2007 | Johnson |
| 2007/0293982 A1 | 12/2007 | Rosenblum |
| 2008/0173705 A1 | 7/2008 | Girard et al. |
| 2008/0195251 A1 | 8/2008 | Milner |
| 2008/0283542 A1 | 11/2008 | Lanka et al. |
| 2009/0048712 A1 | 2/2009 | Rosenblum |
| 2009/0057341 A1 | 3/2009 | Girard et al. |
| 2009/0134181 A1 | 5/2009 | Wachman et al. |
| 2009/0144189 A1 | 6/2009 | Leuthhardt et al. |
| 2010/0324728 A1 | 12/2010 | Rosenblum |

OTHER PUBLICATIONS

U.S. Appl. No. 11/998,461, filed Nov. 29, 2007, Luethardt, et al.
U.S. Appl. No. 12/001,061, filed Dec. 7, 2007, Hyde, et al.
U.S. Appl. No. 12/001,063, filed Dec. 7, 2007, Hyde, et al.
U.S. Appl. No. 12/002,794, filed Dec. 18, 2007, Hyde, et al.
U.S. Appl. No. 12/004,094, filed Dec. 19, 2007, Hyde, et al.
U.S. Appl. No. 12/012,500, filed Feb. 1, 2008, Hyde, et al.
U.S. Appl. No. 12/074,245, filed Feb. 29, 2008, Hyde, et al.

* cited by examiner

STERILIZATION OF CONSUMABLE COMPOSITION DISPENSERS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/998,461, entitled Programmed Dispensing of Consumable Compositions, naming Eric C. Leuthardt, Clarence T. Tegreene, Lowell L. Wood, Jr., Roderick A. Hyde and Robert W. Lord as inventors, filed Nov. 29, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/001,061, entitled Programmed Dispensing of Consumable Compositions, naming Roderick A. Hyde, Eric C. Leuthardt, Robert W. Lord, Clarence T. Tegreene, and Lowell L. Wood, Jr. as inventors, filed Dec. 7, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/001,063, entitled Programmed Dispensing of Consumable Compositions, naming Roderick A. Hyde, Eric C. Leuthardt, Robert W. Lord, Clarence T. Tegreene, and Lowell L. Wood, Jr. as inventors, filed Dec. 7, 2007 now U.S. Pat. No. 7,804,419.

For purposes of the USPTO extra-statutory requirements, the present application constitutes a continuation-in-part of U.S. patent application Ser. No. 12/002,794, entitled Communication Regarding Aspects of a Consumable Composition, naming Roderick A. Hyde, Eric C. Leuthardt, Robert W. Lord, Clarence T. Tegreene, and Lowell L. Wood, Jr. as inventors, filed Dec. 18, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/004,094, entitled Communication Regarding Aspects of a Consumable Composition, naming Roderick A. Hyde, Eric C. Leuthardt, Robert W. Lord, Clarence T. Tegreene, and Lowell L. Wood, Jr. as inventors, filed Dec. 19, 2007, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

BACKGROUND

Programmed regimens of consumable compositions may be prescribed by a physician or may simply be desirable for the health and well-being of an individual. However, confusion may arise concerning the schedule, dosage, and/or compliance with a programmed dosing regimen.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Figure 1:
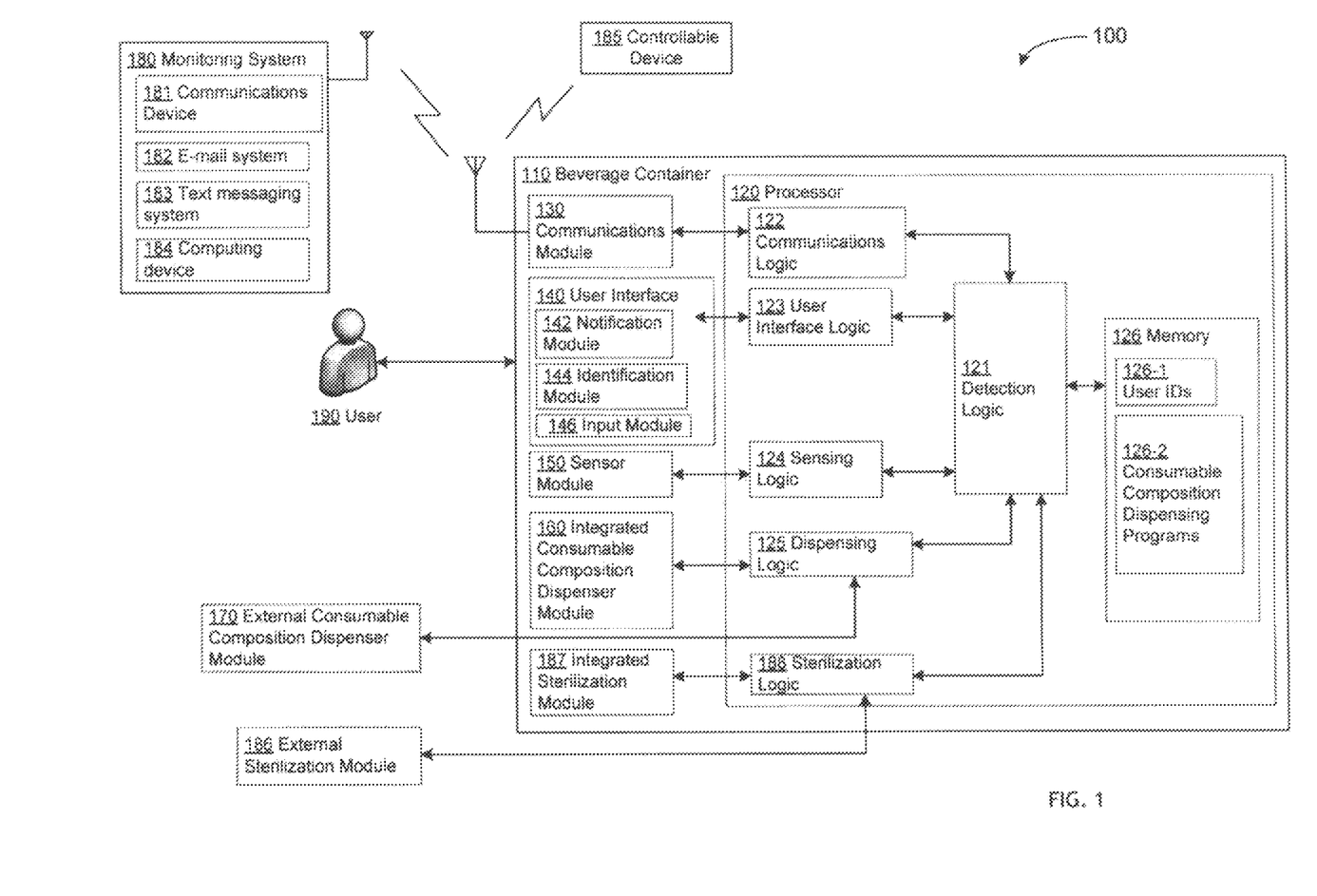
FIG. 1 shows a high-level block diagram of a beverage container.

FIG. 1 illustrates an example environment in which one or more technologies may be implemented. A consumable composition dispensing system 100 may comprise a beverage container 110 to be used by user 190. The beverage container 110 may include any receptacle configured for retaining a liquid or gel composition. For example, the beverage container 110 may include a cup, glass, mug, bowl, pitcher, jug, or the like.

The beverage container 110 may include a processor 120 (e.g. a microprocessor), a communications module 130 (e.g.

a cellular transciever, a Bluetooth transceiver, a WiFi transceiver, a satellite transceiver), a user interface 140 (e.g. display, touchscreen, keypay, speaker system), a sensor module 150 (e.g. a thermometer, barometer, concentration sensor, biometric sensor, accelerometer, UV sensor) an integrated consumable composition dispenser module 160 (e.g. injector, mechanical dispenser) and/or an integrated sterilization module 187 (e.g. a heating element).

The integrated consumable composition dispenser module 160 may be physically incorporated as a component of the beverage container 110. The integrated consumable composition dispenser module 160 may include an acuated mechanical apparatus which opens in response to a command from dispensing logic 125, thereby dispensing a dose of the consumable composition. The beverage container 110 may be configured to receive a dose of the consumable composition via gravitational flow or by pressurized injection of the dispensed composition from the integrated consumable composition dispenser module 160.

The external consumable composition dispenser module 170 may be physically separated from the beverage container 110. The external consumable composition dispenser module 170 may include a mechanical apparatus which opens in response to a command from dispensing logic 125 so as to introduce a dose of the consumable composition into the beverage container 110. The beverage container 110 may be configured to receive a dose of the consumable composition via a communicating assembly whereby the beverage container 110 may be physically coupled to the external consumable composition dispenser module 170 via a mutual conduit operably configured to allow the passage of the consumable composition between the external consumable composition dispenser module 170 and the beverage container 110.

Processor 120 may include communications logic 122, user interface logic 123, sensing logic 124, dispensing logic 125, memory 126, and/or sterilization logic 188.

Memory 126 may include user IDs 126-1 and/or consumable composition dispensing programs 126-2.

User interface 140 may include a notification module 142 (e.g. an LED), an identification module 144 (a fingerprint scanner), and/or an input module 146 (a microphone).

Sensor module 150 may include one or more of a light source sensor, a position sensor, an emission sensor, a spectrophotometer, an infrared or ultraviolet sensor, a biometric sensor and the like. Sensor module 150 may include a biometric sensor which senses the presence of saliva, perspiration, sebum and the like, either on the surface of the beverage container 110 or as a component of the contents therein. Sensor module 150 may include an accelerometer, an inertial motion sensor, and the like, which may sense the movement of the beverage container 110. Sensor module 150 may include a fiber optic pressure sensor, mechanical deflection pressure sensor, strain gauge pressure sensor, piezoresistive pressure sensor, microelectromechanical (MEMS) pressure sensor, variable capacitance pressure sensor, and the like which senses a pressure applied to the beverage container 110. Sensor module 150 may include a capacitive concentration sensor which may sense a concentration of the consumable composition present in the beverage container 110. Sensor module 150 may include an inclinometer and the like. Sensor module 150 may include a flowmeter for sensing a flowrate into or out of the beverage container 110. Sensor module 150 may include a capacitive level sensor, such as a strip or dual-probe sensor (e.g., a strip running down that side of the cup to sense a fluid level based at least in part between differences in the known/inferred/assumed dielectric constants of air and a fluid). In some instances, the dielectric constant is recalled/calcuated in response to a sensed composition of a fluid (e.g., sensed constituents of an alcoholic cocktail); in other instances, the dielectric constant is assumed (e.g., defaults to that of water). Sensor module 150 may include an electrochemical analyzer (e.g. an electrode pair disposed within an electrolyte capable of measuring an electrochemical reaction) for measuring a concentration of a gas in an atmosphere.

The consumable composition dispensing system 100 may further include an external consumable composition dispenser module 170 (e.g. injector, mechanical dispenser) and/or external sterilization module 186 (e.g. an autoclave).

Monitoring system 180 may relay a notification (e.g. a notification that a sterilization of the beverage container 110 has occured) received from communications module 130 to a communications device 181 (e.g. a cell phone, satellite phone, Blackberry®, and/or land-line phone), e-mail system 182 (e.g. an IMAP, POP3, SMTP, and/or HTTP e-mail server having an e-mail account associated with a user 190), text messaging system 183 (e.g. SMS system in GSM) and/or a computing device 184 (e.g. a personal digital assistant (PDA), personal computer, laptop, music player and/or gaming device).

Figure 2:
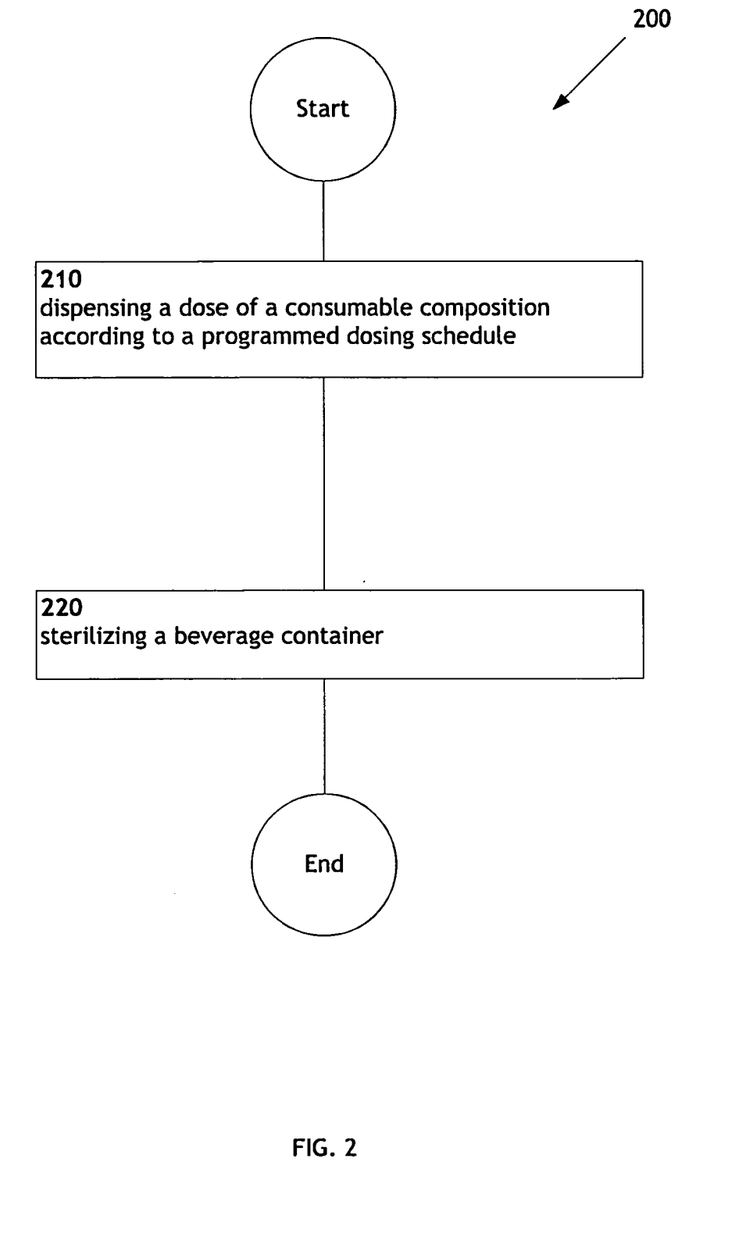
FIG. 2 is a high-level logic flowchart of a process.

FIG. 2 illustrates an operational flow 200 representing example operations related to programmed dispensing of consumable compositions. In FIG. 2 and in following figures that include various examples of operational flows, discussion and explanation may be provided with respect to the above-described examples of FIG. 1, and/or with respect to other examples and contexts. However, it should be understood that the operational flows may be executed in a number of other environments and contexts, and/or in modified versions of FIG. 1. Also, although the various operational flows are presented in the sequence(s) illustrated, it should be understood that the various operations may be performed in other orders than those which are illustrated, or may be performed concurrently.

Further, in FIG. 2 and in following figures, various operations may be depicted in a box-within-a-box manner. Such depictions may indicate that an operation in an internal box may comprise an optional example embodiment of the operational step illustrated in one or more external boxes. However, it should be understood that internal box operations may be viewed as independent operations separate from any associated external boxes and may be performed in any sequence with respect to all other illustrated operations, or may be performed concurrently.

After a start operation, the operational flow 200 moves to a dispensing operation 210, where dispensing a dose of a consumable composition according to a programmed dosing schedule may occur (e.g. distributing a pharmaceutical composition in accordance with a user or physician-defined regimen). For example, as shown in FIG. 1, integrated consumable composition dispenser module 160, and/or external consumable composition dispenser module 170 may distribute doses (e.g. 30 mg) of a consumable composition (e.g. Paxil) into a beverage container 110 (e.g. a cup).

The consumable composition may be a pharmaceutical composition including, but not limited to, one or more of the following: 5-alpha reductase inhibitors, 5-HT antagonists, ACE inhibitors, adrenergic agonists, adrenergic neurone blockers, alkalising agent, alpha blockers, aminoglycosides, anaesthetics, analgesics, androgens, angiotensin receptor blockers, anti-allergics, antiandrogens, antianginals, antiarrhythmics, antibiotics, anticholinergics, anticholinesterase, anticoagulants, anticonvulsants, antidepressants, antidiarrhoeals, antidopaminergics, anti-emetics, antiepileptics, antiflatulents, antifungal, antifungals, anti-hemophilics, antihistamine, antihistamines, antiplatelets, antipsychotics, antiseptics, antispasmodic, antispasmodics, antithyroid drugs, antitussives, anxiolytics, astringents, barbiturates, benzodiazepine, beta-receptor antagonists, beta-receptor blocker, bile acid sequestrants, bronchodilators, calcitonins, calcium channel blockers, cannabinoids, carbonic anhydrase inhibitors/hyperosmotics, cardiac glycosides, cerumenolyti, cholinergics, corticosteroids, COX-2 selective inhibitors, cycloplegics, cyclopyrrolone, cytoprotectants, decongestants, diphosponates, diuretics, dopamine antagonist, emetic, fibrinolytics, fluoroquinolones, gonadotropins, growth hormones, H2-receptor antagonists, haemostatic drugs, heparins, hormonal contraceptives, hypnotics, hypolipidaemic agents, imidazoles, immunoglobulins, immunosuppressants, insulin, interferons, laxatives, local anesthetics, mast cell inhibitors, miotics, monoclonal antibodies, movement disorder drugs, mucolytics, muscle relaxants, mydriatics, neuromuscular drugs, nitrates, nitroglycerin, NSAIDs, ocular lubricants, opioids, parasympatholytics, parasympathomimetics, peripheral activators, polyenes, prostaglandin agonists/prostaglandin inhibitors, prostaglandin analogues, proton pump inhibitors, quinolones, reflux suppressants, selective alpha-1 blocker, sildenafil, statins, steroids, stimulants, sulfa drugs, sympathomimetics, thyroid hormones, topical anesthetics, topical antibiotics, vaccines, vasoconstrictors, vasodilators, vasopressin analogues, or the like.

The consumable composition may be a neutraceutical composition including, but not limited to, one or more of the following: vitamins (e.g., ascorbic acid, pyridoxine, riboflavin), minerals (e.g., calcium salts, zinc salts, potassium salts), hormones (e.g., dimethylaminoethanol (DMAE), dehydroepiandrosterone (DHEA), melatonin), biochemicals (e.g., adenosine triphosphate, coenzyme A, cysteine), glandulars (e.g., edible compositions derived from glandular organs of animals such as the thyroid, pancreas, adrenal cortex), herbals (e.g., ginkgo, garlic, goldenseal, echinacea), or the like.

Then, in a sterilization operation 220, sterilizing at least a portion of a beverage container may occur (e.g. the extermination or deactivation of at least one transmissible agent such as fungi, bacteria, viruses, prions, spores, and the like from the surface or contents of the beverage container 110). For example, as shown in FIG. 1, an integrated sterilization module 187 may be operably coupled to the beverage container 110. Further, the beverage container 110 may be placed in proximity to an external sterilization module 186. The integrated sterilization module 187 and/or the external sterilization module 186 may be operably coupled to sterilization logic 188 which may be configured to cause the integrated sterilization module 187 and/or the external sterilization module 186 to sterilize the beverage container. Further, the external sterilization module 186 may be controlled internally and independent from the sterilization logic 188. The manner, duration, and/or scheduling of the sterilization may be selected according to a sterilization parameter such as: a time interval since a prior sterilization (e.g. sterilize every 3 hours), a user input (e.g. a "sterilize"input from user input 146), an amount of consumable composition in a consumable compostion dispenser (e.g. sterilize when internal consumable composition dispenser module 160 is empty), a time interval in which the beverage container 110 remains in a substantially stationary position (e.g. sterilize with a ultraviolet sterilization when an accelerometer sensor in sensor module 150 indicates the beverage container has not be moved for 5 hours and sterilize with chemical sterilization when the beverage container 110 has not been moved for 10 hours), an identity of a first consumable composition previously dispensed into the beverage container 110 (e.g. sterilize for 10 seconds for solid based consumable compositions and sterilize for 30 seconds for liquid-based consumable compositions), an identity of a second consumable to be dispensed into the beverage container 110 in the future (sterilze for 5 minutes prior to dispensing a second consumable composition which is contraindicated for a previously dispensed consumable composition), a geographic location (e.g. multiple sterilizations when beverage container is determined to be in an undeveloped geographic region), ambient environmental conditions (e.g. extended sterilization when temperature, pressure, and humidity conditions are conducive to transmissible agents), programmed sterilization schedule (e.g. sterilize according to programmed consumable composition dosing schedule), and/or a user identity (e.g. sterilze between uses by different users).

Figure 3:
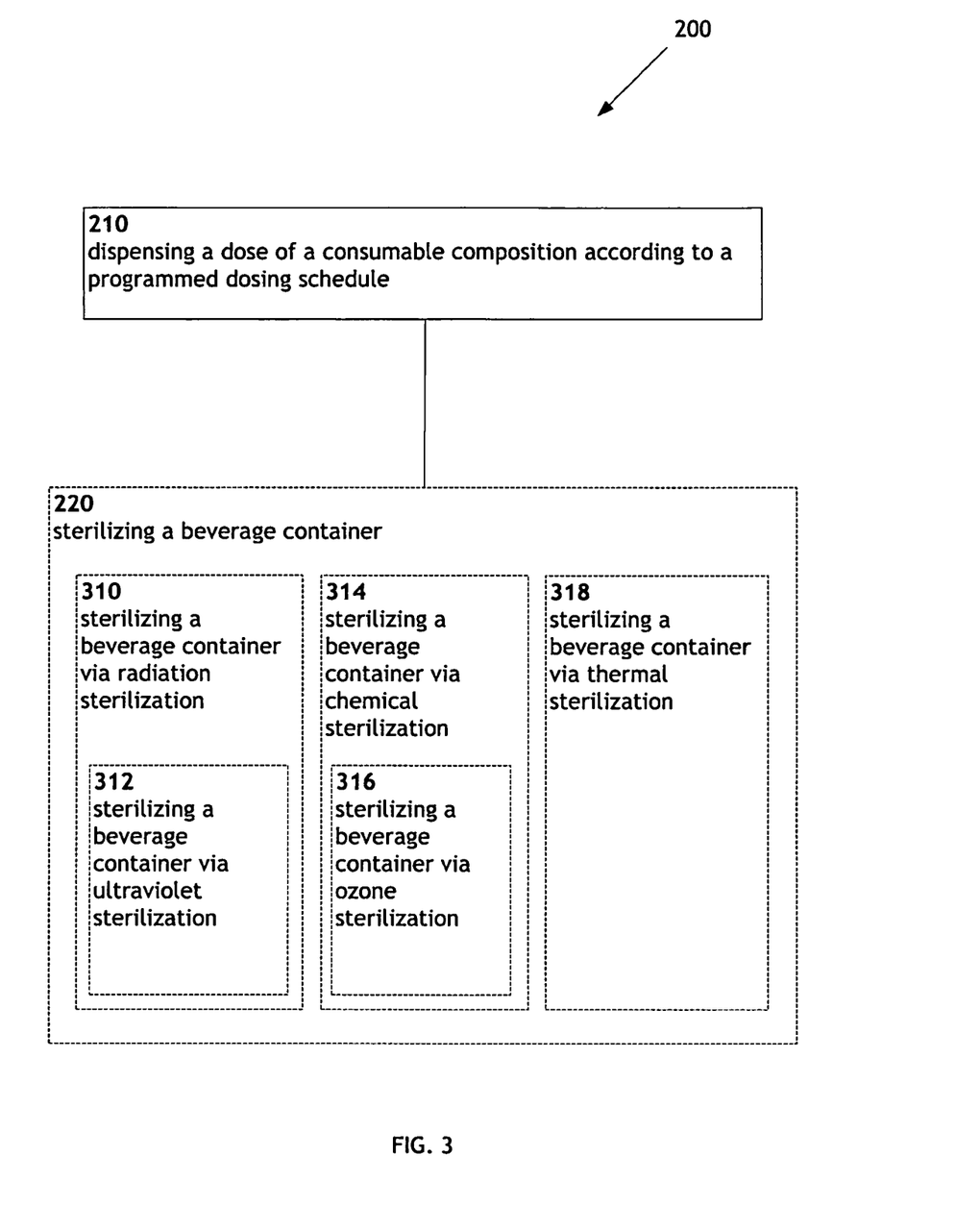
FIG. 3 is a high-level logic flowchart of a process depicting alternate implementations of FIG. 2.

FIG. 3 illustrates alternative embodiments of the example operational flow 200 of FIG. 2. FIG. 3 illustrates example embodiments where the sterilizing operation 302 may include at least one additional operation. Additional operations may include an operation 310, an operation 312, an operation 314, an operation 316, and/or an operation 318.

At the operation 310, sterilizing a beverage container via radiation sterilization may occur (e.g. irradiating the beverage container 110 with a dose of gamma-ray radiation). For example, the integrated sterilization module 187 and/or the external sterilization module 186 may be a radiation steriliazation module that may generate non-ionizing radiation (e.g. ultraviolet, visible light, infrared), ionizing radiation (e.g. x-rays, gamma rays) and/or sub-atomic particle radiation (e.g. alpha radiation, beta radiation, neutron radiation). The sterilization logic 188 may cause the integrated sterilization module 187 and/or the external sterilization module 186 to irradiate the beverage container 110.

At the operation 312, sterilizing a beverage container via ultraviolet sterilization may occur (e.g., illumination of an ultraviolet lamp). For example, as shown in FIG. 1, the integrated sterilization module 187 and/or the external sterilization module 186 may be an ultraviolet sterilization module. Sterilization logic 188 may cause the integrated sterilization module 187 and/or the external sterilization module 186 to emit a dose of ultraviolet radiation towards at least a portion of the beverage container 110.

At the operation 314, sterilizing a beverage container via chemical sterilization may occur (e.g. immersion of the beverage container 110 in a solution containing a surfactant). For example, the integrated sterilization module 187 and/or the external sterilization module 186 may be a chemical sterilization module that may dispense a chemical sterilization agent (e.g. ozone, ethylene oxide, chlorine bleach, surfactants, glutaraldehyde, formaldehyde, ortho-phthalaldehyde, hydrogen peroxide, iodine, sodium hydroxide). The chemical sterilization agent may be allowed to contact at least a portion of the surface of the beverage container 110. Further, the external sterilization module 186 may comprise a liquid bath or gas chamber which may receive the beverage container 110. The sterilization logic 188 may cause the integrated sterilization module 187 and/or the external sterilization module 186 to dispense the chemical sterilization agent.

At the operation 316, sterilizing a beverage container via ozone sterilization may occur (e.g. dispensing an amount of ozone gas into a gas chamber containing a beverage container). For example, as shown in FIG. 1, the integrated sterilization module 187 and/or the external sterilization module may be an ozone sterilization module. Sterilization logic 188 may cause the integrated sterilization module 187 and/or the external sterilization module 186 to generate and/or dispense a quantity of ozone.

At the operation 318, sterilizing a beverage container via thermal sterilization may occur (e.g. forced-ventilation dry heating of a beverage container). For example, as shown in FIG. 1, the integrated sterilization module 187 and/or the external sterilization module 186 may be a thermal sterilization module and may comprise a heating element (e.g. ceramic coated wire, heat lamp, positive thermal coefficient (PTC) ceramics) which may irradiate at least a portion of the beverage container 110 with thermal energy. Further, the integrated sterilization module 187 and/or the external sterilization module 186 may comprise a steam generation mechanism (e.g. an autoclave) which may generate and/or dispense steam which may contact at least a portion of the beverage container. The integrated sterilization module 187 and/or the external sterilization module 186 may comprise a pressurization mechanism such that at least a portion of the beverage container may be maintained at an elevated pressure before, during, and/or after thermal sterilization.

Figure 4:
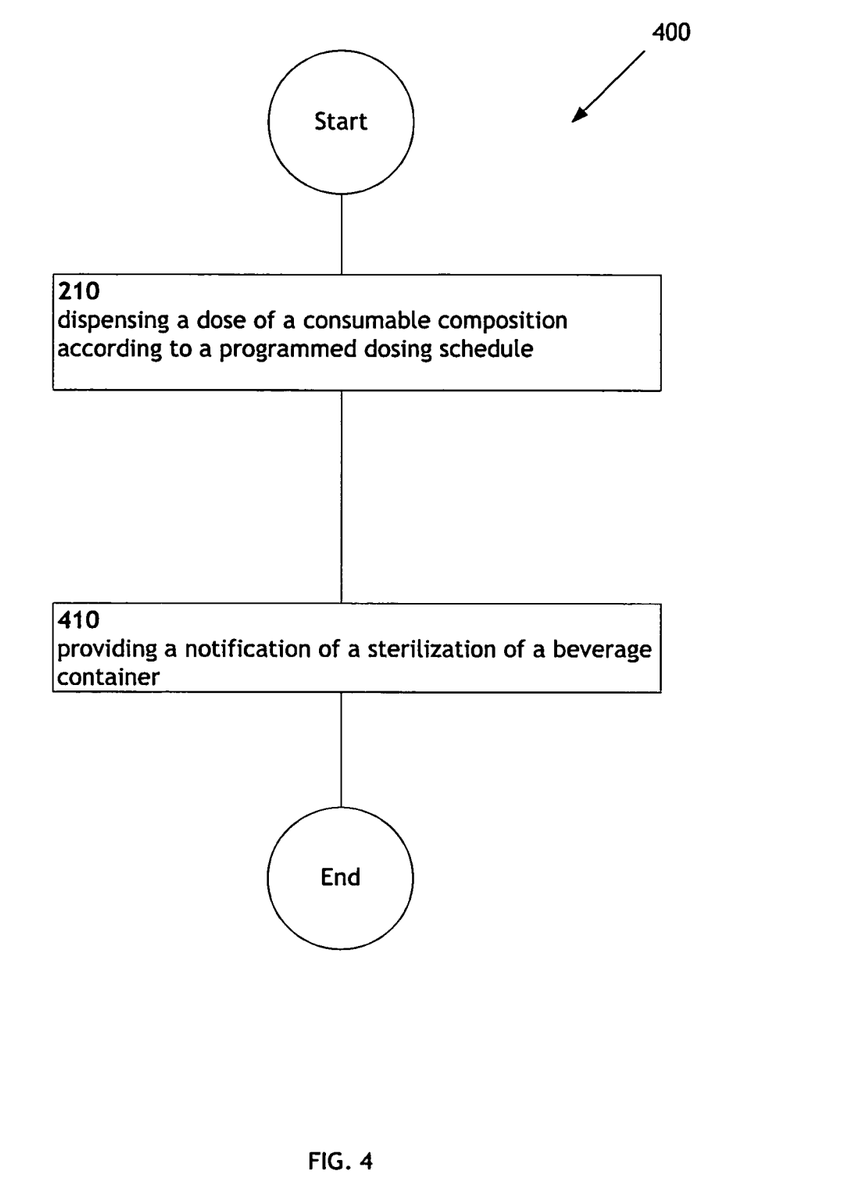
FIG. 4 is a high-level logic flowchart of a process.

FIG. 4 illustrates an operational flow 400 representing example operations related to programmed dispensing of consumable compositions. After a start operation and a dispensing operation 210, the operational flow 400 may move to a sterilization notification operation 410 where providing a notification of a sterilization of a beverage container may occur (e.g. illuminating a green LED upon detection of a thermal sterilization). For example, as shown in FIG. 1, sterilization logic 188 may provide sterilization data to detection logic 121. Detection logic 121 may provide notification data to user interface logic 123. User interface logic 123 may cause the notification module 142 of the user interface 140 to provide a notification of a sterilization of the beverage container 110 to a user 190.

Figure 5:
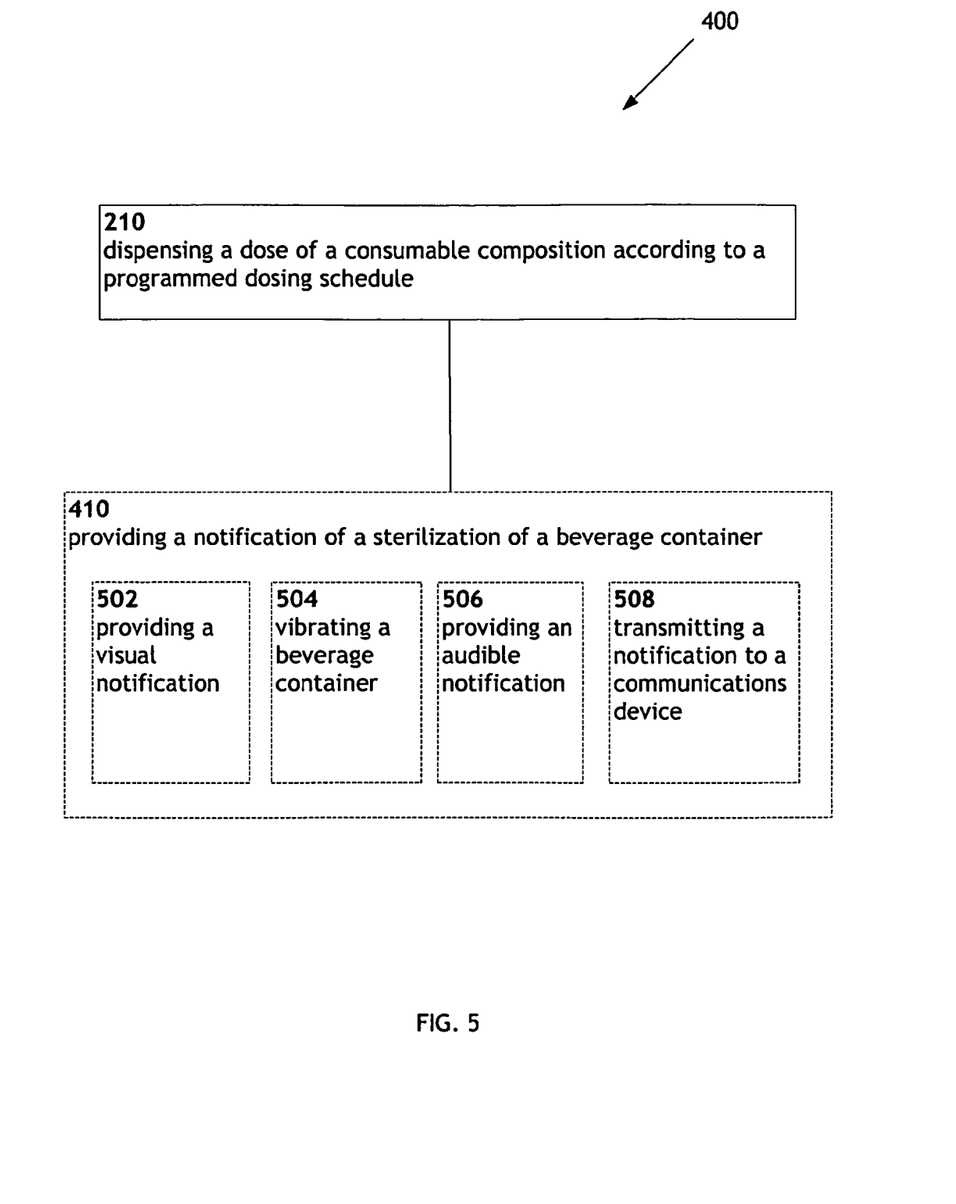
FIG. 5 is a high-level logic flowchart of a process depicting alternate implementations of FIG. 4.

FIG. 5 illustrates an example embodiment where the example operational flow 400 of FIG. 4 may include at least one additional operation. Additional operations may include an operation 502, an operation 504, an operation 506 and/or an operation 508.

At the operation 502, providing a visual notification may occur (e.g. a graphical notice on a display screen). For example, as shown in FIG. 1, the notification module 142 of the user interface 140 may be a visual notification module and may include illuminated LEDs, an LCD or LCoS display screen displaying text, images and/or icons, and the like.

At the operation 504, vibrating a beverage container may occur (e.g. movement of an asymmetrical mass). For example, as shown in FIG. 1, the notification module 142 of the user interface 140 may be a vibrating notification module and may include an asymmetrical rotating mass operably coupled to a motor. Upon application of power to the motor by user interface logic 123, the mass may be rotated such that it induces vibration in the beverage container 110. Further, the notification module 142 of the user interface 140 may include a periodically oscillating mass operably coupled to a spring mechanism. The user interface logic may cause a spring support (e.g. a lever) to retract allowing for the oscillation of the mass.

At the operation 506, providing an audible notification may occur (e.g. an audio broadcast of a ring tone). For example, as shown in FIG. 1, the notification module 142 of the user interface 140 may be an audible notification module and may include a speaker assembly, and the like. The user interface logic 123 may cause the notification module 142 to emit an audible notification (e.g. a mechanical ringing of a bell, a synthesized or recorded vocal notification such as "Your beverage container has been sterilized by ozone sterilization", an electronic beep).

At the operation 508, transmitting a notification to a communications device may occur (e.g. placing an automated call to a user's home phone). For example, as shown in FIG. 1, the communications module 130 may transmit a sterilization notification (e.g. a text message, an instant message, an automated voicemail, an automated phone call) to a monitoring system 180 linked to a communications device 181. The communications device 181 may include a cell phone, satellite phone, Blackberry®, land-line phone, and the like.

Monitoring system 180 may relay a notification (e.g. a notification that a sterilization of the beverage container 110 has occured) received from communications module 130 to a communications device 181 (e.g. a cell phone, satellite phone, Blackberry®, and/or land-line phone), e-mail system 182 (e.g. an IMAP, POP3, SMTP, and/or HTTP e-mail server having an e-mail account associated with a user 190), text messaging system 183 (e.g. SMS system in GSM) and/or a computing device 184 (e.g. a personal digital assistant (PDA), personal computer, laptop, music player and/or gaming device).

Figure 6:
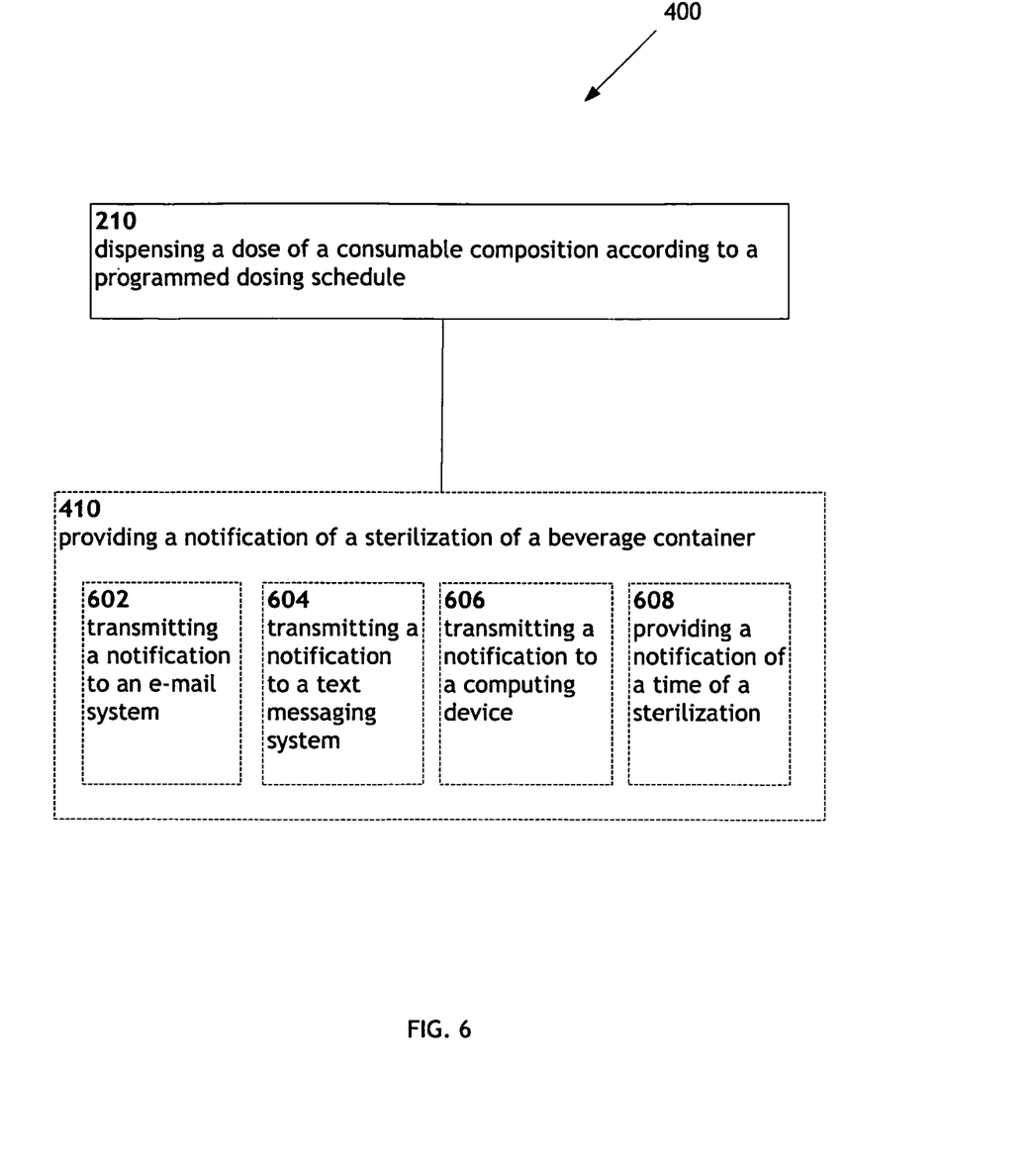
FIG. 6 is a high-level logic flowchart of a process depicting alternate implementations of FIG. 4.

FIG. 6 illustrates alternative embodiments of the example operational flow 400 of FIG. 4. FIG. 6 illustrates example embodiments where the notification operation 410 may include at least one additional operation. Additional operations may include an operation 602, an operation 604, an operation 606, and/or an operation 608.

At the operation 602, transmitting a notification to an e-mail system may occur (e.g an e-mail to an IMAP, POP3, SMTP, and/or HTTP e-mail server having an e-mail account associated with a user 190). For example, as shown in FIG. 1, the communications module 130 may transmit a sterilization notification to a monitoring system 180 linked to an e-mail system 182.

At the operation 604, transmitting a notification to a text messaging system may occur (e.g. an automated text message to a user's cell phone). For example, as shown in FIG. 1, the communications module 130 may transmit a notification to a monitoring system 180 linked to a text messaging system 183 such as an SMS system in GSM.

At the operation 606, transmitting a notification to a computing device may occur (e.g. an automated instant message to a user's computer). For example, as shown in FIG. 1, the communications module 130 may transmit a notification (e.g. an instant message to a personal computer, an instant message via an online gaming system, such as the Xbox Live® system marketed by the Microsoft® Corporation, an instant message to a music player via a music download service, such as the iTunes® service marketed by Apple® Inc.) to a monitoring system 180 linked to a computing device 184. The computing device 184 may include a personal digital assistant (PDA), personal computer, laptop, music player, gaming device, and the like capable of receiving instant messages from IM providers such as Microsoft®.

At the operation 608, providing a notification of a time of a sterilization may occur (e.g. a broadcasted audible notification that "A thermal sterilization occurred at 3:30 pm). For example, as shown in FIG. 1, the user interface logic 123 may cause the notification module 142 of the user interface 140 to provide a notification of a time of sterilization of the beverage container 110. The notification module 142 may provide a time interval (e.g. 1 hour, 15 minutes) since the most recent sterilization or until an upcoming sterilization. The notification module may futher provide a notification if a time interval in excess of a threshold sterilization window has elapsed where another sterilization of the beverage container 110 is required before its reuse.

Figure 7:
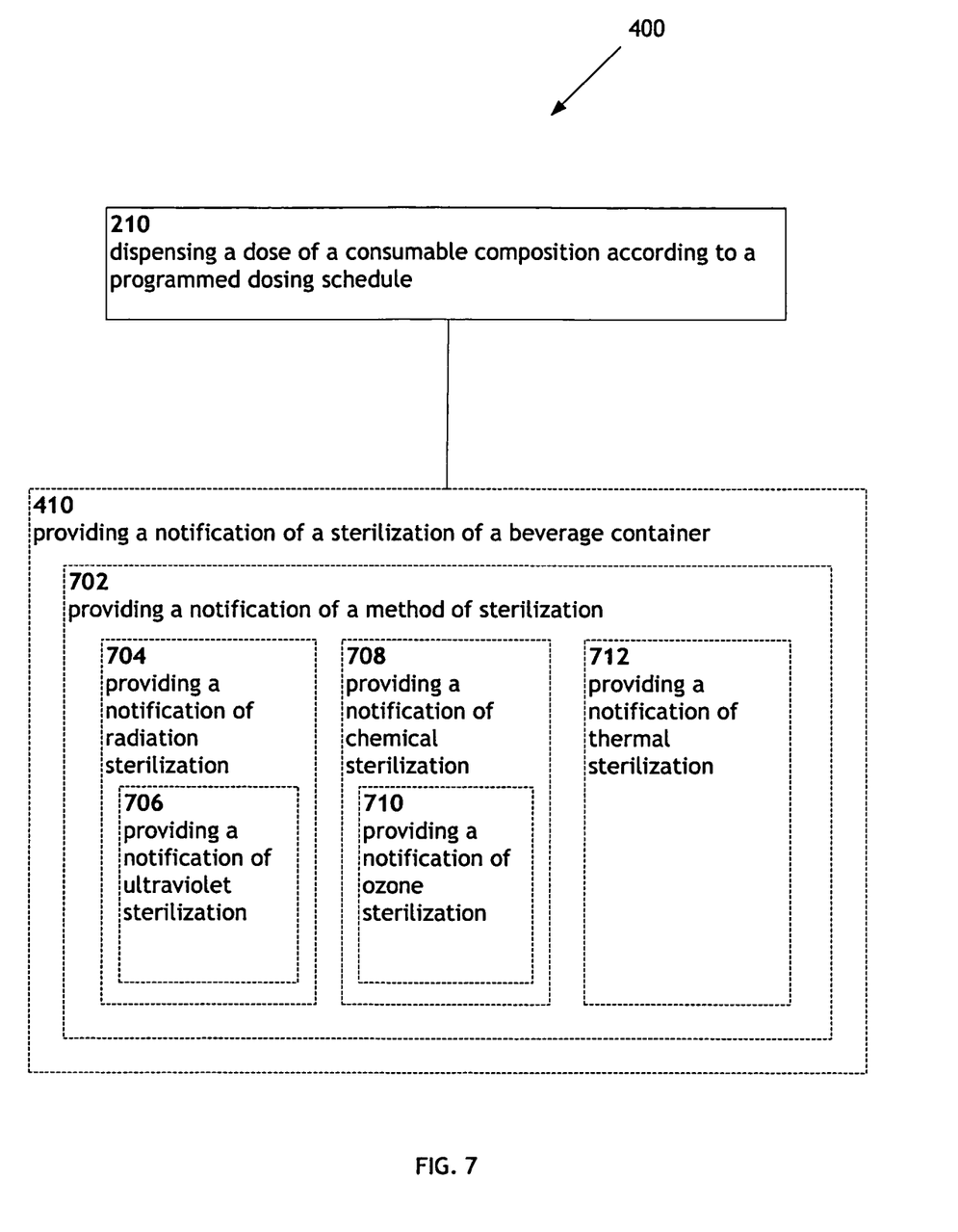
FIG. 7 is a high-level logic flowchart of a process depicting alternate implementations of FIG. 4.

FIG. 7 illustrates alternative embodiments of the example operational flow 400 of FIG. 4. FIG. 7 illustrates example embodiments where the notification operation 410 may include at least one additional operation. Additional operations may include an operation 702, an operation 704, an operation 706, an operation 708, and/or an operation 710.

At the operation 702, providing a notification of a method of sterilization may occur (e.g. an LCD display presenting a text based message stating "An ultraviolet sterilization has been completed"). For example, as shown in FIG. 1, the user interface logic 123 may cause the notification module 142 of the user interface 140 to provide a notification of a method of sterilization of the beverage container 110 to a user 190. Further, the communications logic 122 may cause the communications module 130 to transmit a notification that a sterilization has been detected by the sensor module 150 to the monitoring system 180.

Further, at the operation 704, providing a notification of radiation sterilization may occur (e.g. an e-mail to an e-mail account associated with a user 190 indicating that an ultraviolet sterilization of the beverage container 110 has occured). For example, user interface logic 123 may cause the notification module 142 of the user interface 140 to provide a notification that radiation sterilization of the beverage container 110 has occured. Further, the communications logic 122 may cause the communications module 130 to transmit a notification that radiation sterilization of the beverage container 110 has occured.

Further, at the operation 706, providing a notification of ultraviolet sterilization may occur (e.g. a UV-sensitive indicator patch on the beverage container 110 changes color). For example, user interface logic 123 may cause the notification module 142 of the user interface 140 to provide a notification that the integrated sterilization module 187 has emitted a dose of ultraviolet radiation. Further, the communications logic 122 may cause the communications module 130 to transmit a notification to the monitoring system 180 that an exposure of the beverage container 110 to ultraviolet radiation from the external sterilization module 186 has been detected by the sensor module 150 (e.g. a radiation sensor module).

Further, at the operation 708, providing a notification of chemical sterilization may occur (e.g. an audible ring tone from a speaker assembly that a chemical composition has been dispensed into the beverage container 110). For example, user interface logic 123 may cause the notification module 142 of the user interface 140 to provide a notification that a chemical sterilization of the beverage container 110 has occured. Further, the communications logic 122 may cause the communications module 130 to transmit a notification that chemical sterilization of the beverage container 110 has occured.

Further, at the operation 710, providing a notification of ozone sterilization may occur (e.g. an automated voice mail transmitted to a home phone of a user 190 stating that the beverage container 110 has been exposed to a given concentration of ozone for a threshold period of time). For example, user interface logic 123 may cause the notification module 142 of the user interface 140 to provide a notification that the integrated sterilization module 187 has dispensed a dose of ozone. Further, the communications logic 122 may cause the communications module 13 to transmit a notification to the monitoring system 180 that an exposure of the beverage container 110 to ozone dispensed from the external sterilization module 186 has been detected by the sensor module 150 (e.g. a chemical sensor module).

Further, at the operation 712, providing a notification of thermal sterilization may be provided (e.g. a text message that at least a portion of the beverage container 110 has been maintained at a given temperature for a threshold time interval). For example, user interface logic 123 may cause the notification module 142 of the user interface 140 to provide a notification that the integrated sterilization module 187 has heated the interior of the beverage container for a period of time. Further, the communications logic 122 may cause the communications module 130 to transmit a notification to the monitoring system 180 that an exposure of the beverage container 110 to heat generated by the external sterilization module 186 has been detected by the sensor module 150 (e.g. a thermal sensor module).

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A system for administering a consumable composition, the system comprising:
   a computing device configured for obtaining schedule data specifying a consumable composition dose consumption schedule for a specified user;
   a dispenser device configured for dispensing at least one dose of the consumable composition into a container according to the schedule data specifying the consumable composition dose consumption schedule for the specified user; and
   a sterilization controller device configured for controlling sterilizing of at least a portion of the container.

2. The system of claim 1, wherein the sterilization controller device configured for controlling sterilizing of at least a portion of the container includes:
   a sterilization controller device configured for controlling at least one radiation sterilization device to sterilize at least a portion of the container.

3. The system of claim 2, wherein the sterilization controller device configured for controlling at least one radiation sterilization device to sterilize at least a portion of the container includes:
   a sterilization controller device configured for controlling at least one ultraviolet sterilization device to sterilize at least a portion of the container.

4. The system of claim 1, wherein the sterilization controller device configured for controlling sterilizing of at least a portion of the container includes:
   a sterilization controller device configured for controlling at least one chemical sterilization device to sterilize at least a portion of the container.

5. The system of claim 4, wherein the sterilization controller device configured for controlling at least one chemical sterilization device to sterilize at least a portion of the container includes:
   a sterilization controller device configured for controlling at least one ozone sterilization device to sterilize at least a portion of the container.

6. The system of claim 1, wherein the sterilization module configured for controlling sterilizing of at least a portion of the container includes:
   a sterilization controller device configured for controlling at least one thermal sterilization device to sterilize at least a portion of the container.

7. The system of claim 1, wherein the sterilization controller device configured for controlling sterilizing of at least a portion of the container includes:
   a sterilization controller device configured for controlling sterilizing of at least a portion of the container according to a sterilization parameter.

8. The system of claim 7, wherein the sterilization controller device configured for controlling sterilizing of at least a portion of the container according to a sterilization parameter includes:
   a sterilization module configured for sterilizing at least a portion of the container according to a time interval since a prior sterilization of the container.

9. The system of claim 7, wherein the sterilization controller device configured for controlling sterilizing of at least a portion of the container according to a sterilization parameter includes:
   a sterilization controller device configured for controlling sterilizing of at least a portion of the container in response to a user input.

10. The system of claim 7, wherein the sterilization controller device configured for controlling sterilizing of at least a portion of the container according to a sterilization parameter includes:
    a sterilization controller device configured for controlling sterilizing of at least a portion of the container according to an amount of the consumable composition in the consumable composition dispenser.

11. The system of claim 7, wherein the sterilization controller device configured for controlling sterilizing of at least a portion of the container according to a sterilization parameter includes:
    a sterilization controller device configured for controlling sterilizing of at least a portion of the container according to a time interval in which the container remains in a substantially stationary position.

12. The system of claim 7, wherein the sterilization controller device configured for controlling sterilizing of at least a portion of the container according to a sterilization parameter includes:
    a sterilization controller device configured for controlling sterilizing of at least a portion of the container according to an identity of the consumable composition.

13. The system of claim 7, wherein the sterilization controller device configured for controlling sterilizing of at least a portion of the container according to a sterilization parameter includes:
    a sterilization controller device configured for controlling sterilizing of the container according to a geographic location of the container.

14. The system of claim 7, wherein the sterilization controller device configured for controlling sterilizing of at least a portion of the container according to a sterilization parameter includes:
    a sterilization controller device configured for controlling sterilizing of at least a portion of the container according to one or more ambient environmental conditions of the container.

15. The system of claim 7, wherein the sterilization controller device configured for controlling sterilizing of at least a portion of the container according to a sterilization parameter includes:
    a sterilization controller device configured for controlling sterilizing of at least a portion of the container according to a programmed sterilization schedule.

16. The system of claim 7, wherein the sterilization controller device configured for controlling sterilizing of at least a portion of the container according to a sterilization parameter includes:
    a sterilization controller device configured for controlling sterilizing of at least a portion of the container according to a user identity.

17. The system of claim 1, wherein the sterilization controller device configured for controlling sterilizing of at least a portion of the container further comprises:
  a sterilization controller device configured for controlling sterilizing of one or more contents of the container.

18. The system of claim 1, wherein the sterilization controller device configured for controlling sterilizing of at least a portion of the container includes:
  a sterilization controller device configured for controlling sterilizing of at least a portion of the container at least partially in response to the dispensing of the at least one dose of the consumable composition into the container.

* * * * *

UNITED STATES PATENT AND TRADEMARK OFFICE
CERTIFICATE OF CORRECTION

| | | |
|---|---|---|
| PATENT NO. | : 8,758,677 B2 | Page 1 of 1 |
| APPLICATION NO. | : 12/006252 | |
| DATED | : June 24, 2014 | |
| INVENTOR(S) | : Hyde et al. | |

It is certified that error appears in the above-identified patent and that said Letters Patent is hereby corrected as shown below:

In the Claims

In Column 14, Lines 22-23, Claim 10 please delete text "...the consumable composition dispenser" and replace with --the dispenser device--

Signed and Sealed this
Second Day of June, 2015

Michelle K. Lee
*Director of the United States Patent and Trademark Office*